United States Patent
Iske et al.

(10) Patent No.: US 9,931,451 B2
(45) Date of Patent: Apr. 3, 2018

(54) MULTIFUNCTIONAL HANDLE OF A BLOOD TREATMENT MACHINE FOR MOVING THE BLOOD TREATMENT MACHINE BY HAND AND FOR COILING CABLES AND A BLOOD TREATMENT MACHINE WITH SUCH A HANDLE

(71) Applicant: B. BRAUN AVITUM AG, Melsungen (DE)

(72) Inventors: Andreas Iske, Soehrewald (DE); Bruno Stenzel, Muenden (DE)

(73) Assignee: B. BRAUN AVITUM AG, Melsungen (DE)

( * ) Notice: Subject to any disclaimer, the term of this patent is extended or adjusted under 35 U.S.C. 154(b) by 0 days.

(21) Appl. No.: 14/965,381

(22) Filed: Dec. 10, 2015

(65) Prior Publication Data
US 2016/0175504 A1    Jun. 23, 2016

(30) Foreign Application Priority Data
Dec. 18, 2014   (DE) ......................... 10 2014 119 107

(51) Int. Cl.
| | | |
|---|---|---|
| F16M 13/00 | (2006.01) | |
| A61M 1/14 | (2006.01) | |
| H05K 5/02 | (2006.01) | |
| B62B 3/10 | (2006.01) | |
| B62B 5/06 | (2006.01) | |

(52) U.S. Cl.
CPC .............. *A61M 1/14* (2013.01); *B62B 3/102* (2013.01); *B62B 5/06* (2013.01); *H05K 5/023* (2013.01); *A61M 2205/502* (2013.01); *A61M 2209/08* (2013.01); *A61M 2209/082* (2013.01); *A61M 2209/084* (2013.01)

(58) Field of Classification Search
USPC ....................................... 248/58, 61, 301, 303
See application file for complete search history.

(56) References Cited

U.S. PATENT DOCUMENTS

| | | | | |
|---|---|---|---|---|
| 5,005,790 A * | 4/1991 | Harris, III | ............ | B65H 75/366 248/213 |
| 6,079,675 A * | 6/2000 | Hsu | .......................... | B65G 7/12 248/68.1 |
| 8,245,985 B2 * | 8/2012 | Goetz | .................. | A01G 25/165 137/624.11 |

(Continued)

FOREIGN PATENT DOCUMENTS

| | | |
|---|---|---|
| DE | 102011010249 | 8/2012 |
| EP | 0 240 153 | 10/1987 |
| WO | 2004028594 | 4/2004 |

OTHER PUBLICATIONS

European Search Report (with translation) for EP 15199476 dated Apr. 21, 2016.

(Continued)

*Primary Examiner* — Steven M Marsh
(74) *Attorney, Agent, or Firm* — RatnerPrestia (57) ABSTRACT

A multifunctional handle for a blood treatment machine for moving the blood treatment machine by hand and also for the coiling of cables, with a placement segment and a slip prevention segment which protrudes from a first end of the first flat section at an angle from the first flat section and which is designed ergonomically to be grasped by a hand.

20 Claims, 4 Drawing Sheets

(56) References Cited

U.S. PATENT DOCUMENTS

| | | |
|---|---|---|
| 9,004,433 B2 * | 4/2015 | Krieger .................. B60N 3/102 |
| | | 108/165 |
| 9,101,703 B2 | 8/2015 | Foerger |
| 9,166,385 B2 * | 10/2015 | Newman .................. H02G 1/00 |
| 2009/0012458 A1 | 1/2009 | Childers et al. |
| 2009/0084717 A1 | 4/2009 | Delmage et al. |
| 2010/0089806 A1 | 4/2010 | Peters et al. |
| 2011/0040242 A1 | 2/2011 | Fallon et al. |

OTHER PUBLICATIONS

German Search Report for German Application No. 10 2014 119 107.2 dated Jun. 29, 2015, including full translation.

\* cited by examiner

MULTIFUNCTIONAL HANDLE OF A BLOOD TREATMENT MACHINE FOR MOVING THE BLOOD TREATMENT MACHINE BY HAND AND FOR COILING CABLES AND A BLOOD TREATMENT MACHINE WITH SUCH A HANDLE

CROSS REFERENCE TO RELATED APPLICATIONS

This application claims priority to German Application No. DE 10 2014 119 107.2 filed Dec. 18, 2014, the contents of such application being incorporated by reference herein.

FIELD OF THE INVENTION

This invention concerns a multifunctional handle of a mobile machine for extracorporeal blood treatment or mobile blood treatment machine for moving the blood treatment machine by hand and for coiling cables and a blood treatment machine with such a multifunctional handle.

BACKGROUND OF THE INVENTION

Modern extracorporeal blood treatment, such as dialysis, is becoming increasingly complex and versatile. Based on an increasingly broad range of technical innovations and additional treatment devices, it has been possible to continuously raise the standard of clinical blood treatment in the course of recent years. However, the increasing number of new technical devices also means there is growing pressure to make more efficient use of the construction space available in blood treatment machines so as to be able to house more and more technical functions in a preferably mobile blood treatment machine of conventional size. In addition to the miniaturization of components and other technical elements of the blood treatment machine, the conception of multifunctional components has a key role to play here.

DESCRIPTION OF THE RELATED ART

A conventional blood treatment machine is known from WO 2004/028594A1, for example. Such a mobile blood treatment machine has on its outside a number of separate components which allow movement of the dialysis machine by hand (two handles), coiling or stowage of fluid lines or cables (a clip) and protection of the various electrical or IT interfaces of the dialysis machine from splash water (a raised edge on the tray-like top of the dialysis machines or cover flaps for the interfaces). Frequently, conventional blood treatment machines, especially those of the mobile kind, additionally comprise stopper elements which protrude from the corpus of the blood treatment machine and are intended to prevent damage to the corpus or housing of the dialysis machine caused by collisions with walls, for instance, while the dialysis machine is being shifted.

These numerous separate components take up a large amount of construction space in the design of such a blood treatment machine, and this space is therefore no longer immediately available for components which are directly relevant to dialysis itself. Due to the limited construction space, the various components such as the clip for coiling cables cannot be placed in an optimum position, so the cables coiled on the clip will often cover electrical interfaces and IT interfaces or obstruct operation of the dialysis machine.

What is more, unnecessary assembly effort is required in the manufacture of such dialysis machines, which is why the production costs of such dialysis machines are relatively high.

SUMMARY OF THE INVENTION

Based on the state of the art described above, an object of the invention is to provide a blood treatment machine, preferably a dialysis machine of the mobile kind, which is characterized by more efficient use of construction space, lower production costs and less assembly effort. In particular, a single multifunctional handle is to perform the functions of moving or shifting the preferably mobile blood treatment machine and the stowage or coiling of cables or tubes connected to the blood treatment machine, as well as preferably also acting as a stopper for the blood treatment machine or protecting it in the event of potential collisions and protecting various electrical interfaces and IT interfaces of the blood treatment machine.

This object is achieved by a multifunctional handle with the features according to the independent claim and by a blood treatment machine, preferably a blood treatment machine, with such a multifunctional handle. Advantageous embodiments of the invention are the subject of the dependent claims.

The core idea of the present invention is therefore to combine several functions or purposes in a single multifunctional component, in particular a multifunctional handle. The multifunctional handle according to aspects of the invention therefore has at least two (structural) functional segments, one of which is structurally designed to take/hold cables/tubes and the other for ergonomic grasping by an operating individual. According to aspects of the invention, the two functional segments are not adaptively but integratively connected to one another in such a way that each functional segment contributes to performing the function of the other.

In other words, a handle usually has a more or less ergonomically shaped grip segment which has to be kept apart from a housing wall or other such component by a spacer so as to be able to be firmly grasped in its entirety. According to a first aspect of the invention, this spacer is now shaped as a cable/tube holder (holder/suspension segment for cables/tubes), whereby the grip segment simultaneously forms a retention/block element that prevents the cable/tube suspended on the cable/tube holder from slipping/falling off over the latter's free end. In addition, the grip segment can be shaped/positioned in such a way that it at least partially frames the housing wall or similar component in the manner of a buffer bar, thereby providing protection from collisions.

According to the independent claim, therefore, a multifunctional handle of a mobile blood treatment machine, preferably a (hemo-)dialysis machine, is proposed for moving the blood treatment machine by hand and for the coiling or suspension of cables and/or tubes, the multifunctional handle comprising a bracket-like or groove-like cable holder segment and an ergonomically shaped grip segment which is positioned or configured at at least one end portion of the bracket-like or groove-like cable holder segment. This means that the multifunctional handle (or multifunction handle), in addition to providing an ergonomically shaped grip geometry, also offers a holder optimized for hanging up flexurally flexible cables, this holder in turn keeping the grip geometry apart from the blood treatment machine in such a way that it can be grasped by an operating individual. This integrative design of the multifunctional handle means that adaptive fittings such as additional hooks mounted on the handle or additional protrusions on the handle as hanging facilities, for example in the shape of pegs, are superfluous. The relevant shape of the cable holder segment and the positioning of the grip segment are also critical in ensuring that cables/tubes already suspended cannot be unintentionally knocked off.

According to a particularly preferred embodiment, the multifunctional handle comprises a slip prevention segment which is positioned between the bracket-like or groove-like cable holder segment and the ergonomically shaped grip segment and which is arched in such a way towards the mobile blood treatment machine that the cables and/or tubes placed in the bracket-like or groove-like holder segment are prevented from slipping off. This configuration of the multifunctional handle allows particularly simple and safe stowage of tubes on the handle. The handle according to aspects of the invention is therefore not such that it can simply be used for an unintended purpose, instead it is specifically designed to be suitable for this second function, without suffering disadvantages in the fulfillment of its first/main purpose.

Another preferred embodiment of the invention provides for the grip segment to be shaped in the manner of a handrail or bar, extending longitudinally in a cable holding direction defined by the cable holder segment. In this way, the handle can be extended to shoulder width, for example, so as to be able to apply sufficient manual force to be able to move the blood treatment machine.

Provision can preferably be made for the grip segment to be positioned at at least one end (front side) of the cable holder segment located transversely to the cable holding direction. In this case, therefore, the grip is preferably separated into two handle sections which are positioned on the two front sides of the cable holder segment, viewed in the cable holding direction, and which enclose the cable holder segment in between them. Alternatively, provision can also be made for the grip segment to be positioned at an end of the cable holder segment located longitudinally to the cable holding direction. This end can be point-shaped in the case of a bracket-type structure and edge-shaped in the case of a groove-type structure.

According to another potentially independent aspect of the present invention, provision can be made for the cable holder segment of the multifunction handle to be tightly connected or connectable to the mobile blood treatment machine (hemodialysis machine), at the connection end of the cable holder segment that is opposite to the grip segment, preferably with a connector or mounting adaptor. In this way, a suspended cable/tube is stowed between the grip segment and the blood treatment machine and thereby secured from slipping off. Preferably, the cable holder segment of the multifunctional handle serves as a spacer between the grip segment and the blood treatment machine.

Furthermore, provision can be made for the preferably handrail-like or bar-like grip segment to protrude over the cable holder segment at at least one end and preferably at both its longitudinal ends, viewed in the cable holding direction. In this way, the grip segment not only performs the function of applying the manual force of an operating individual to the machine but also protects the machine/machine housing from impact damage.

It can be advantageous if the cable holder segment is arched in a cup-like manner viewed in the cable holding direction so as to avoid bending of the cables and/or tubes suspended. Preferably, the cable holder segment is configured as a flat, preferably panel-like component. In this way it offers a flat placement surface which means that damage to the cables/tubes can be prevented.

For the purpose of simple and inexpensive production, the multifunctional handle can preferably be combined with a connector or mounting adaptor and made from a single piece of material, either metal or plastic.

Finally, another aspect of the present invention concerns provision of a blood treatment machine preferably with a machine housing on which a multifunctional handle according to aspects of the invention is mounted.

It can be seen from the above description of the invention that the multifunctional handle, due to its bracket or groove type, forms the tube holder segment or placement segment around which cables are coiled for stowage purposes and preferably forms a slip prevention area connected to the placement segment, the slip prevention area protruding at an angle from the placement segment at the latter's free end portion, thereby preventing cables stowed on the placement segment from slipping off the latter's free end portion. The distinctive nature of the multifunctional handle according to aspects of the invention lies in the fact that the slip prevention segment is created by an at least partially ergonomic design for grasping by a hand, whereby the functions "easy/ergonomic grasp" and "prevention of coiled cables from slipping off" are combined in a single structural segment of the multifunctional handle. In addition, the placement segment of the multifunctional handle can be configured as a preferably flat segment protruding from the corpus/component or housing of the blood treatment machine (hemodialysis machine), which also acts as a kind of protruding (arched) roof to protect electrical sockets and/or IT interfaces positioned on the housing of the machine from splash water. In this way, it is possible to combine the functions "stowage of cables" and "protection from splash water" in a single structural segment of the multifunctional handle.

The configuration of the multifunctional handle according to the independent claim is therefore based on the design concept that each structural segment of the handle is to be designed in such a way, as far as possible, that the one structural segment is suited to performing as many different functions as possible, thereby enabling the functionality of the multifunctional handle as a whole to be extended to include as broad a range of functions as possible.

The multifunctional handle according to this invention enables the assembly effort and production costs of a preferably mobile blood treatment machine such as a hemodialysis machine to be reduced, because rather than having to mount separate components to perform the functions "shifting", "stowage", "stopper" and "protection of sensitive interfaces", only a single component is required, namely the multifunctional handle according to aspects of the invention. The more efficient use of installation space also means increased flexibility in the technical configuration of the blood treatment machine (hemodialysis machine). For example, the tray-like top of the machine no longer requires a raised edge, which can obstruct the handling of objects placed on the top, since protection of the machine's sensitive electrical and IT interfaces is already taken care of by the multifunctional handle.

Finally it should be pointed out that the tube holder segment/placement segment does not necessarily have to be configured as a flat surface (panel) but can also comprise at least one bar from which a slip prevention segment in the form of a second bar protrudes at a defined angle, thereby defining the bracket-type structure. For an improved grasp, the slip prevention segment can, for instance, comprise a grip ball or a grip bar or handrail at the (free) end of the bar facing away from the placement segment. Another alternative is for the placement segment and the slip prevention segment of the multifunctional handle to be structurally integrated in a single curved bar or panel (hook-shaped). In this case, the curvature of the bar determines the angle between the placement segment and the slip prevention segment of the multifunctional handle.

In an advantageous embodiment, the angle between the placement segment and the slip prevention segment is essentially a right angle. The result of this is essentially an L-shaped handle (in cross section).

Advantageously, this configuration involves the placement segment of the multifunctional handle protruding at right angles from the corpus or housing of the blood treatment machine and the slip prevention segment protruding essentially at right angles from the placement segment towards the top of the blood treatment machine, so that a kind of recess/groove is formed between the slip prevention segment and the top surface of the corpus or housing of the blood treatment machine. When the ergonomically shaped slip prevention segment for shifting the mobile blood treatment machine is grasped, the recess/groove is located behind the slip prevent segment from the point of view of the person grasping the multifunctional handle. Since the recess/groove serves to hold cables, this configuration is particularly advantageous, since in this way the cables placed in the recess/groove and coiled around the placement segment of the multifunctional handle do not hinder the grasping of the slip prevention segment of the multifunctional handle.

Alternatively, the slip prevention segment of the multifunctional handle can be permanently fixed to the surface of the corpus/housing of the blood treatment machine on its side facing away from the placement segment, preferably with a connector. In the case of such a back-to-back connection between the multifunctional handle and the corpus of the blood treatment machine, the placement segment of the multifunctional handle forms a placement surface for coiled cables which, from the point of view of an individual grasping the multifunctional handle, is situated in front of the slip prevention segment. In order to prevent the cables placed on the placement surface and coiled around the placement segment of the multifunctional handle from slipping off, this preferred embodiment can involve the end of the placement segment facing away from the slip prevention segment being curved upwards, i.e. in the direction of the top of the blood treatment machine, thereby serving as a second, additional slip prevention segment. In this case, the handle would approximate a U shape in cross section.

One advantage of the configurations of the multifunctional handle on the corpus of a blood treatment machine as described lies in the fact that the placement segment essentially protrudes from the corpus or housing of the blood treatment machine at a right angle. If sensitive electrical interfaces or IT interfaces are positioned on the corpus of the blood treatment under the placement segment of the multifunctional handle viewed from the top of the blood treatment machine, the protruding placement segment protects the electrical or IT interfaces from falling splash water in the manner of an overhanging roof. As a result of the design of the multifunctional handle, therefore, there is no necessity for separate covers to be provided for these interfaces.

What is more, since the multifunctional handle also serves as a stopper element, i.e. protecting the blood treatment machine in the event of collisions rather like a buffer bar, there is likewise no necessity for a separate stopper element.

Furthermore, according to an advantageous variation of the multifunctional handle, shifting the mobile blood treatment machine is facilitated by the grip bar protruding over the placement segment in the direction of placement at at least one of its ends. It is especially advantageous if the grip bar or handrail protrudes over the placement segment at both ends by the same length, since this configuration facilitates shifting of the mobile blood treatment machine to both the right and the left.

According to another advantageous configuration, at least one of the placement segment and the slip prevention segment of the multifunctional surface is curved in design. For example, the placement segment which forms the recess/groove or placement surface to hold cables is configured as the shell of a half-cylinder. Such a configuration prevents the cables from slipping off or falling from the placement surface or recess/groove. The slip prevention segment rising from the placement segment can be arched in such a way that it forms a convex curvature of the surface of the corpus of the blood treatment machine, for example. Additionally or alternatively, the slip prevention segment can be configured as a shell of a half-cylinder which is convexly curved towards the surface of the corpus or housing of the blood treatment machine. In the case of such a design, cables stowed between the slip prevention segment and the surface of the corpus of the blood treatment machine are wedged in by the curvature of the slip prevention segment, thereby preventing them from falling out of their stowage position.

What is more, the reduction of the number of small parts on the blood treatment machine has advantages in terms of hygiene: the multifunctional handle creates large, flat, rounded and gap-free surfaces that are easy to clean. This is essential in the course of hectic everyday hospital work since surfaces frequently have to be cleaned but there is often limited time available to do so.

In order to further improve efficiency in the use of installation space of the blood treatment machine, the multifunctional handle can also be used as a platform to integrate other components and interfaces required for dialysis. For example, ventilation devices or IT interfaces or sockets can be integrated in the multifunctional handle. The multifunctional can comprise rails along its length (in holding direction), for example, which serve as mount for a ventilator fleece. This creates more ways of configuring the ventilation system as advantageously as possible and making optimum use of the installation space available. Also various sockets, for example to connect various cables, can preferably be located on the side ends or bottom of the multifunctional handle.

In addition to that, the multifunctional handle can further comprise an integrated media strip preferably located/arranged below the cable holder segment at the corpus of the blood treatment machine. This arrangement causes the cable holder segment to screen/protect the various terminals and interfaces from splash water coming from above. Herein the multifunctional handle is preferably configured in such a way that the various terminals are accessible, even if cables are coiled on the cable holder segment.

According to a preferred embodiment the cable holder segment is configured in such a way that it forms a hollow space at its lower face. For example, the cable holder segment is formed arched or as a section of a cylinder surface convexly arched upwards. This geometric form of the cable holder segment creates at the lower face of the multifunctional handle a hollow space bounded by the multifunctional handle at three sides. In this hollow space a functional member, such as a ventilation nonwoven-sheet, may be arranged. This has the advantage that the multifunctional handle protects/screens the ventilation nonwoven-sheet on three sides from undesired touching with the fingers or from other damaging influences. Furthermore, the access route to the ventilation nonwoven-sheet is very contorted, whereby the probability of e.g. undesired touching of the ventilation nonwoven-sheet is further reduced.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1A:
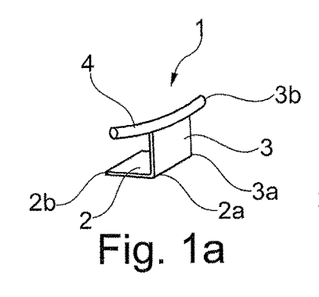
FIG. 1a to 1f show various design examples of a multifunctional handle according to aspects of the invention, each with a bracket-like or groove-like cable holder segment (hereinafter subdivided into placement area/segment and slip prevention area/segment) and an ergonomically shaped grip segment.

FIG. 1a shows the first preferred embodiment of a multifunctional handle 1 for a blood treatment or dialysis machine for moving the dialysis machine by hand and for coiling cables and/or tubes, with a flat or panel-shaped placement area/segment 2 and a flat or panel-shaped slip prevention area/segment 3, which protrudes from a first edge-like end 2a of the placement segment 2 at an angle to the placement segment 2. The segments 2 and 3 go together to form a groove that is V-shaped or L-shaped in cross section combining to form a cable holder segment of the multifunction handle.

In this preferred embodiment, the multifunctional handle 1 is produced as a single piece and the angle between the placement segment 2 and the slip prevention segment 3 is essentially a right angle, though it can be an acute or an obtuse angle. Due to the essentially right-angled configuration, the essentially L-shaped handle 1, of which the surface of the placement segment 2 forms the only placement surface for cables, which can be stowed by being coiled around the handle 1, whereby solely the slip prevention segment 3 is to prevent any unintentional slipping of the already coiled cables/tubes over the free edge of the placement segment 2.

At its free (edge-shaped) end 3b facing away from the placement segment 2, the slip prevention segment 3 comprises a grip bar or handrail 4 for improved grasping of the handle 1 and for simplified shifting of the mobile dialysis machine to which the multifunctional handle 1 is attached, the grip bar or hand rail 4 running along the edge of end 3b of the slip prevention segment 3 facing away from the placement segment 2. The grip bar 4 protrudes at both its ends over the slip prevention segment 3 by an equal length. This enables simple shifting of the mobile dialysis machine to the right and left and also protects the housing of the dialysis machine in the event of collisions.

The surface of the entire multifunctional handle 1 is made up of large, gap-free surfaces free of undercuts and with rounded corners. This simplifies cleaning of the handle 1. Furthermore, it prevents damage to the coiled cables/tubes caused by buckling or crushing, for example.

The multifunctional handle 1 can be connected to the dialysis machine at the second end 2b (facing away from the slip prevention segment 3) of the support segment 2, preferably with a connector/adaptor. With this configuration, the placement surface for cables formed by the placement segment 2 is between the surface of the dialysis machine and the slip prevention segment 3 with the handrail/grip bar 4 on it. Since a user grasps the multifunctional handle 1 by the grip bar 4, the placement surface is located behind the grip bar 4, from the point of view of the person grasping the handle, and any cables situated on the placement surface therefore not obstruct grasping of the multifunctional handle 1 by the grip bar 4.

Alternatively, the multifunctional handle 1 can also be connected to the dialysis machine via the surface formed by the slip prevention segment 3 by way of a back-to-back connection. In this configuration, the placement surface formed by the placement segment 2 is situated in front of the grip bar 4, from the point of view of the person grasping. Such a configuration can potentially facilitate the coiling of cables around the multifunctional handle 1 since the cables do not have to be passed around the grip bar. However, in this case it would be recommended to select a V or U shape for the cable holder area instead of the above-described L shape so as to prevent the coiled cables from slipping off unintentionally in this case, too.

The slip prevention segment 3 can be straight or curved in shape according to FIG. 1a, so that the slip prevention segment 3 replicates the curve of a surface of the dialysis machine on which the multifunctional handle 1 is mounted.

Figure 1B:
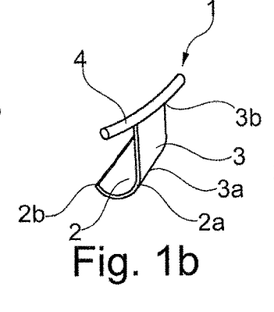

FIG. 1b shows a multifunctional handle 1 according to aspects of the invention on which the placement segment 2 is rounded in shape per se (barrel-shaped), thereby forming a holder recess/groove for improved holding of cables. The reference numerals used in the other figures refer to the same or very similar components.

The rounded shape of the placement segment 2 allows the multifunctional handle 1 to be more compact in design so that the multifunctional handle 1 protrudes from the dialysis machine by less of a distance than a comparable multifunctional handle 1 in which the placement segment 2 is flat in shape, as shown in FIG. 1a. In addition, the slip prevention segment 3 can be curved in shape, so that the slip prevention segment 3 replicates the curve of a surface of the dialysis machine on which the multifunctional handle 1 is mounted.

Figure 1C:
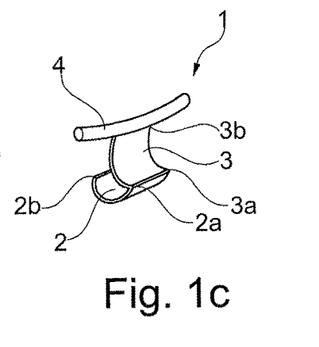

FIG. 1c shows a further embodiment of a multifunctional handle 1 according to aspects of the invention on which the surface of the slip prevention segment 3 is rounded towards the surface of the placement segment 2 (barrel-shaped). In the embodiment shown in this figure, the surface of the placement segment 2 is rounded in shape as in FIG. 1b so that a deeper holder recess/groove is formed. Alternatively, the surface of the placement surface 2 can also be flat, however (not shown). Due to the rounded design of the slip prevention segment 3 according to FIG. 1c, unintentional falling of the cables situated in the placement recess can be prevented in particular in the configuration of the multifunctional handle 1 in which the multifunctional handle 1 is connected to the dialysis machine via the second (edge-shaped) end 2b of the placement segment 2 facing away from the slip prevention segment 3, since the cables are wedged in, as it were, between the curve of the slip prevention segment 3 and the surface of the dialysis machine.

Figure 1D:
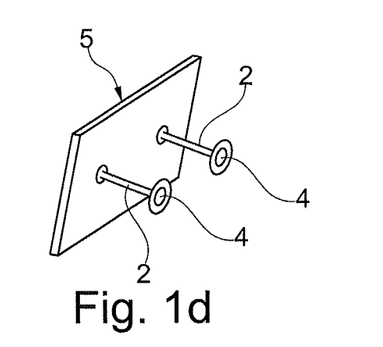
Figure 1E:
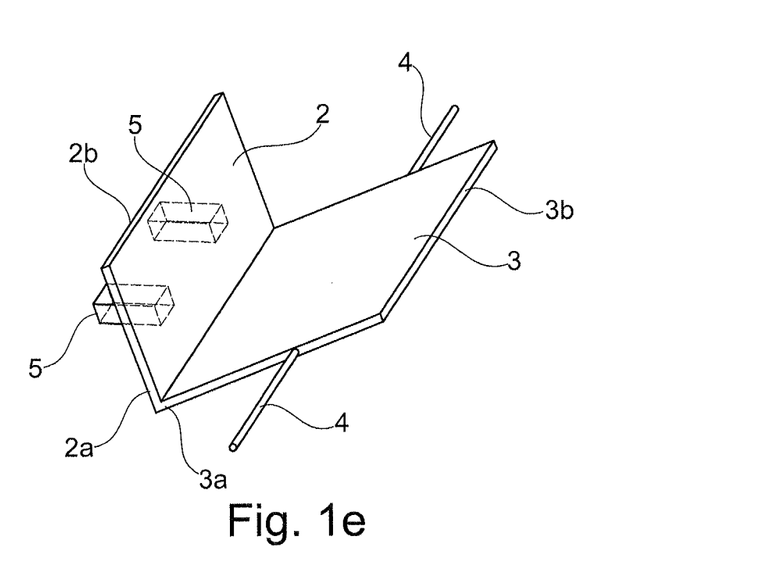

FIG. 1e shows an alternative configuration of the embodiment according to FIG. 1a. In this case, the grip bar 4 is not positioned immediately at the free (edge-shaped) end 3b of the cable holder segment/area but in its central section. The grip bar 4 is structured in two parts, each of which is attached to a front edge of the cable holder segment/area, viewed in the direction of placement/coiling, thereby holding the cable holder segment/area between them. This variant has the advantage that two different cables/tubes can be hung up, for example, which can be separated from each other by the dual-section grip bar 4.

Figure 1F:
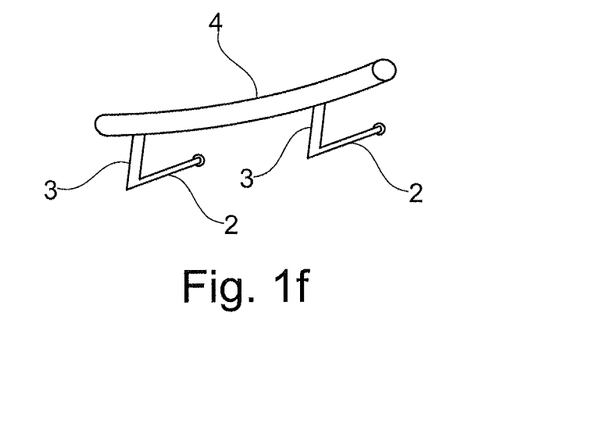

At this point it should be noted that the cable holder segment/area does not necessarily have to be panel-shaped but can also be bar-shaped, as shown in FIGS. 1d and 1f. In this case, the placement segment 2 and/or the slip prevention segment 3 are formed from at least one bar. In this case, the handle can comprise a grip bar 4, as shown in FIG. 1f, or else one or two grip balls/knobs can be positioned at the free bar ends, which at the same time define the slip prevention segment 3. This variant is shown in FIG. 1d.

Figure 2:
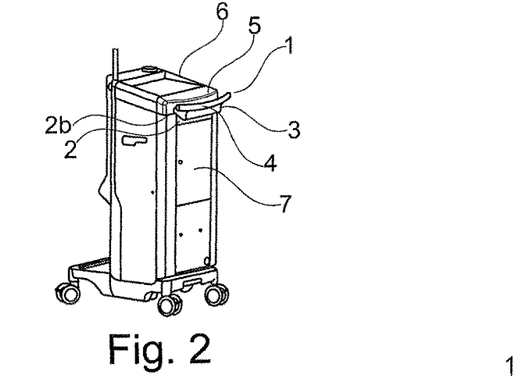
FIG. 2 shows a blood treatment machine (hereinafter always referred to as a dialysis machine) on which the multifunctional handle according to aspects of the invention is mounted with a connector or adaptor.

FIG. 2 shows a blood treatment machine/(hemo-)dialysis machine 6 on which a multifunctional handle 1 according to aspects of the present invention is mounted via a connector 5. Here the multifunctional handle 1 is connected to the second (edge-shaped) end 2b of the placement segment 2 facing away from the slip prevention segment 3 via the connector 5, which is fixedly mounted on the dialysis machine. In this configuration, the placement surface or groove for cables formed by the placement segment 2 is located between the grip bar 4 or the slip prevention segment 3 and the surface of the dialysis machine 6. The handle is therefore the same as the handle described above according to FIG. 1a.

In this depiction, it can be clearly seen how the placement segment 2 of the multifunctional grip 1 protruding from the surface of the dialysis machine 6 protects the flank/side wall 7 of the dialysis machine 6 from splash water falling from above like an overhanging roof. If electrical or IT interfaces are positioned on the flank 7 of the dialysis machine 6 that is protected in this way by the protruding multifunctional handle 1, there is no need for separate covers to protect these interfaces from splash water.

In this configuration, the assembly module consisting of the multifunctional handle 1 and the connector 5 is made of a single piece of material. However, the multifunction handle 1 can also be conceived as a universal handle, which can then be combined with different connectors/adaptors 5 for different blood treatment machines.

Figure 3:
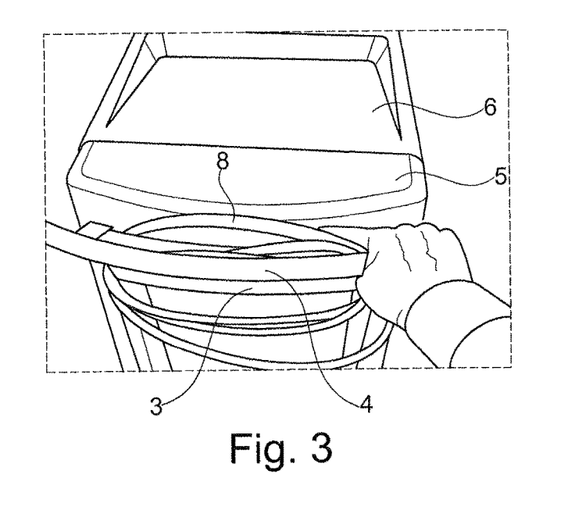
FIG. 3 shows the dialysis machine according to FIG. 2 with the multifunctional handle according to aspects of the invention on which cables or tubes are coiled.

FIG. 3 shows a detailed view of a multifunctional handle 1 which is mounted on a dialysis machine 6. In this depiction, the parts of the assembly module consisting of multifunctional handle 1 and connector 5 which can be seen are the slip prevention segment 3 and the grip bar 4 of the multifunctional handle 1, and also the connector 5. The placement segment 2 of the multifunctional handle 1 is situated underneath the cables 8 coiled on the multifunctional handle 1 and is therefore not visible in this depiction. A user grasps the grip bar 4 at its right-hand end, protruding over the slip prevention segment 3 of the multifunctional handle 1. From the point of the person grasping the multifunctional handle 1, the cables 8 are situated behind the grip bar 4 and therefore do not obstruct grasping of the grip bar 4.

The slip prevention segment 3 and the grip bar 4 are curved in shape so that the curve of the surface replicates the surface of the dialysis machine 6 or the connector 5. Here the multifunctional handle 1 also serves as a stopper element for the dialysis machine 6, since it acts like a buffer bar and protects the housing of the dialysis machine 6 in the event of a collision with walls and the like.

Figure 4A:
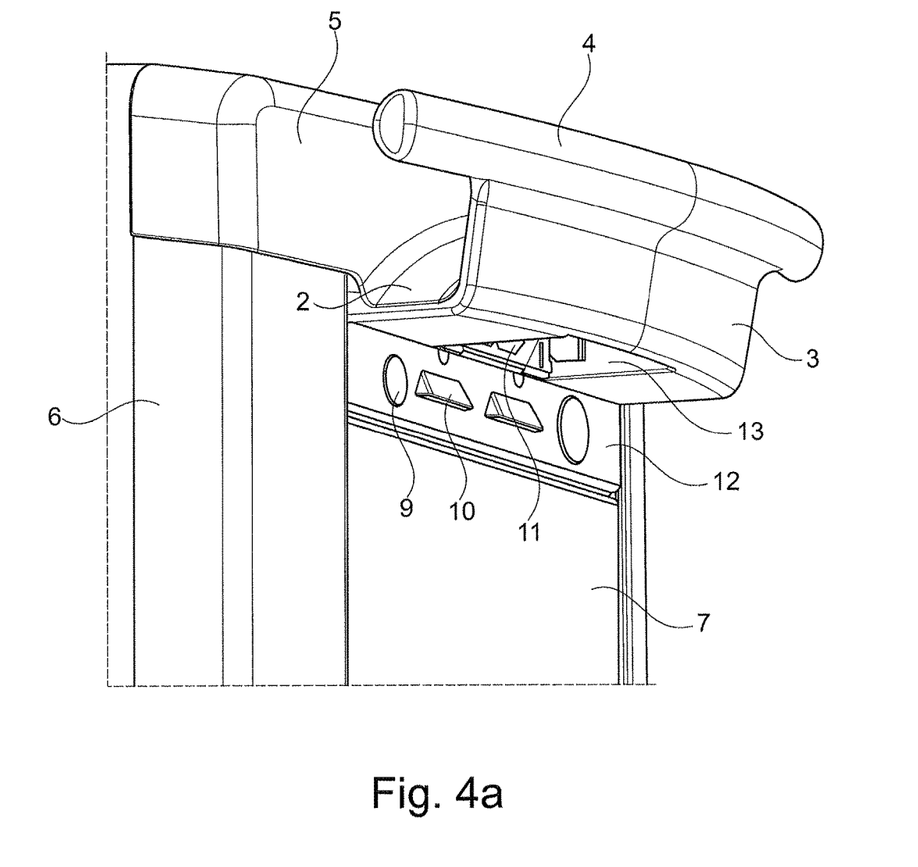
FIGS. 4a and b each show a detailed view from a different viewing angle of a multifunctional handle according to another embodiment of the invention mounted to a dialysis machine and comprising an integrated media strip with electrical interfaces and IT-interfaces as well as a hollow space for protecting/screening a ventilation nonwoven-sheet.

FIG. 4a shows a detailed view of a multifunctional handle 1 according to a further embodiment of the invention that is mounted to a blood treatment machine or dialysis machine 6 and comprises an integrated media strip 12 with electrical interfaces or IT-interfaces 9. In addition to that, the multifunctional handle also has openings 10. These openings 10 serve for example to reduce the dampening of the signal of a speaker mounted in the blood treatment machine, as the sound emitted by the speaker can exit the blood treatment machine to the outside through the openings 10.

The media strip is arranged at the flank 7 of the blood treatment machine 6 that is protected by the multifunctional handle from splash water coming from above behind/under the multifunctional handle 1 when viewed from the top of the blood treatment machine 6. In this configuration the cable holder segment 2 of the multifunctional handle 1 is formed as a section of a cylinder surface that is convexly arched towards the top of the blood treatment machine 6. This geometric configuration of the cable holder segment 2 of the multifunctional handle 1, a hollow space 13 is created at the lower face of the cable holder segment 2 of the multifunctional handle 1. In this hollow space a ventilation nonwoven-sheet is arranged by which the interior of the housing is connected to the atmosphere. Because the cable holder segment 2 of the multifunctional 1 bounds the hollow space 13 at three sides (top side, left side, right side), the ventilation nonwoven-sheet 11 is screened/protected from undesired touching with the fingers, splash water and other damaging influences at these three sides. Through this configuration of the multifunctional handle 1 or the arrangement of the multifunctional handle at the dialysis machine 6, the access to the ventilation nonwoven-sheet 11 or any other element arranged in the hollow space 13 is contorted and hence made difficult. This arrangement allows for a further reduction in the probability of undesired touching of the ventilation nonwoven-sheet 11 by the users or personnel.

Access to the electrical interfaces and IT-Interfaces located at the integrated media strip 12 is secured even when cables are coiled on the cable holder segment 2 of the multifunctional handle 1. For this purpose, the cable holder segment 2 of the multifunctional handle 1 is configured in its dimensions and the arrangement of the electrical interfaces and IT-interfaces at the integrated media strip 12 and the openings 10 are configured in such a way that the cables 8 lying on the cable holder segment 2 protrude sufficiently from the multifunctional handle due to their intrinsic stiffness, so that the interfaces 9 and the openings 10 are not obstructed by the cables 8.

Figure 4B:
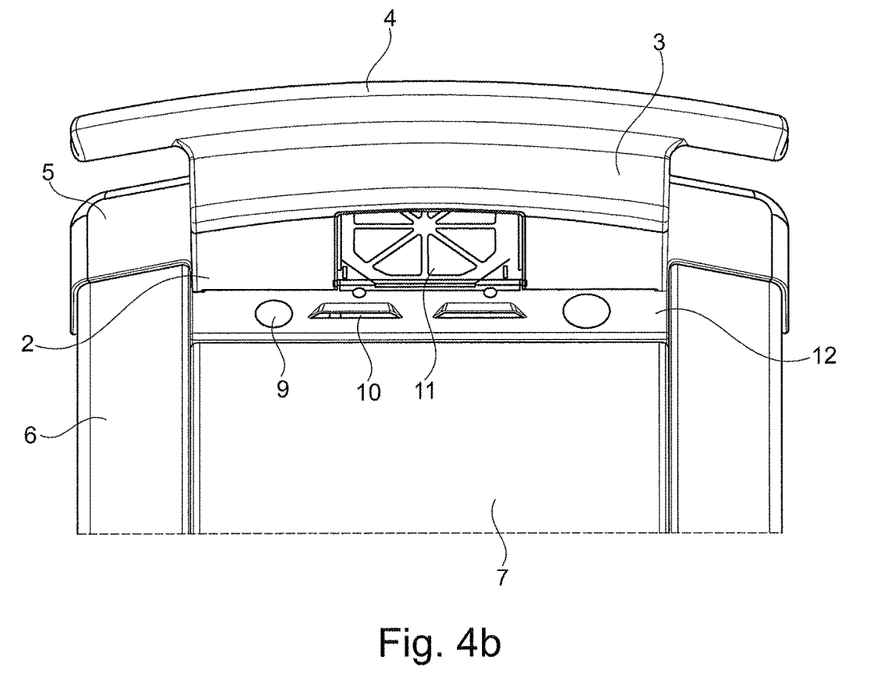

FIG. 4b shows a front view of the multifunctional handle from FIG. 4a.

Accordingly, the ventilation nonwoven-sheet 11 is above the media trip 12 and below the cable holder segment 2 that is arched in a roof-like fashion.

The invention claimed is:
1. A hemodialysis machine comprising:
    a mobile blood treatment machine; and a handle comprising:
  a cable holder segment connected to the mobile blood treatment machine, the cable holder segment configured to support at least one of a cable or a tube,
  an ergonomically shaped grip segment positioned or configured at at least one end portion of the cable holder segment, and
  electrical and other interfaces integrated in an integrated media strip.

2. The hemodialysis machine of claim 1, wherein the cable holder segment is bracket-like.

3. The hemodialysis machine of claim 1, wherein the cable holder segment is groove-like.

4. The hemodialysis machine of claim 1, further comprising a slip prevention segment positioned between the cable holder segment and the ergonomically shaped grip segment, the slip prevention segment arched towards the mobile blood treatment machine such that when the at least one supported cable or tube is placed on the cable holder segment, the at least one supported cable or tube is prevented from slipping off.

5. The hemodialysis machine of claim 1, wherein the grip segment is shaped in the manner of a handrail or bar that extends longitudinally in a cable holding direction defined by the cable holder segment.

6. The hemodialysis machine of claim 5, wherein the grip segment is positioned at an end of the cable holder segment transverse to the cable holding direction.

7. The hemodialysis machine of claim 5, wherein the grip segment is positioned at an end of the cable holder segment longitudinal to the cable holding direction.

8. The hemodialysis machine of claim 1, wherein the cable holder segment is connected or configured to be connected to the mobile blood treatment machine at a connection end opposite the grip segment.

9. The hemodialysis machine of claim 8, wherein the cable holder segment is connected or connectable to the mobile blood treatment machine by a connector or mounting adaptor.

10. The hemodialysis machine of claim 1, wherein the cable holder segment serves as a spacer between the grip segment and the blood treatment machine.

11. The hemodialysis machine of claim 1, wherein the grip segment protrudes over the cable holder segment at at least one end.

12. The hemodialysis machine of claim 11, wherein the grip segment is handrail-like and protrudes over the cable holder segment at both its longitudinal ends in a cable holding direction.

13. The hemodialysis machine of claim 11, wherein the grip segment is bar-like and protrudes over the cable holder segment at both its longitudinal ends in a cable holding direction.

14. The hemodialysis machine of claim 1, wherein the cable holder segment is arched in a cup-like manner in a cable holding direction to prevent bending of the at least one supported cable or tube.

15. The hemodialysis machine of claim 1, wherein the cable holder segment is configured as a flat component or a panel-like component.

16. The hemodialysis machine of claim 1, further comprising a connector or mounting adaptor, wherein the handle is made of a single piece of metal or plastic.

17. The hemodialysis machine of claim 1, wherein the electrical and other interfaces are screened from splash water coming from at least one direction.

18. A hemodialysis machine comprising:
  a mobile blood treatment machine; and
  a handle comprising:
    a cable holder segment connected to the mobile blood treatment machine, the cable holder segment configured to support at least one of a cable or a tube, wherein the cable holder segment provides a hollow space for screening a functional member with a ventilation nonwoven-sheet; and
    an ergonomically shaped grip segment positioned or configured at at least one end portion of the cable holder segment.

19. The hemodialysis machine of claim 17, wherein the handle is mounted at the mobile blood treatment machine such that the handle screens the electrical and other interfaces from splash water coming from a top of the blood treatment machine.

20. The hemodialysis machine blood of claim 18, wherein the handle is mounted to the mobile blood treatment machine such that the handle forms a defined access to the hollow space that is screened at the sides and makes undesired touching of the functional member difficult.

* * * * *